United States Patent
Fram

(10) Patent No.: US 9,460,526 B1
(45) Date of Patent: Oct. 4, 2016

(54) DUAL TECHNIQUE COMPRESSION

(71) Applicant: DR Systems, Inc., San Diego, CA (US)

(72) Inventor: Evan K. Fram, Paradise Valley, AZ (US)

(73) Assignee: D.R. SYSTEMS, INC., San Diego, CA (US)

( * ) Notice: Subject to any disclaimer, the term of this patent is extended or adjusted under 35 U.S.C. 154(b) by 287 days.

(21) Appl. No.: 14/098,399

(22) Filed: Dec. 5, 2013

Related U.S. Application Data

(63) Continuation of application No. 13/359,363, filed on Jan. 26, 2012, now Pat. No. 8,630,501.

(60) Provisional application No. 61/437,236, filed on Jan. 28, 2011.

(51) Int. Cl.
*G06K 9/36* (2006.01)
*G06T 9/00* (2006.01)

(52) U.S. Cl.
CPC .................................... *G06T 9/00* (2013.01)

(58) Field of Classification Search
None
See application file for complete search history.

(56) References Cited

U.S. PATENT DOCUMENTS

| | | | |
|---|---|---|---|
| 5,479,303 A | 12/1995 | Suzuki et al. | |
| 5,555,322 A | 9/1996 | Terai et al. | |
| 5,887,110 A | 3/1999 | Sakamoto et al. | |
| 6,012,091 A | 1/2000 | Boyce | |
| 6,564,004 B1 | 5/2003 | Kadono | |
| 8,184,720 B2* | 5/2012 | Onur | H04N 19/102 348/180 |
| 8,527,649 B2* | 9/2013 | Wexler | H04L 65/4076 709/203 |
| 2002/0061184 A1 | 5/2002 | Miyamoto | |
| 2002/0071663 A1 | 6/2002 | O'Donnel | |
| 2003/0043905 A1 | 3/2003 | Nakayama et al. | |
| 2005/0091696 A1* | 4/2005 | Wolfe | H04N 21/234309 725/116 |
| 2006/0136597 A1* | 6/2006 | Shabtai | H04L 29/06027 709/231 |
| 2006/0195884 A1* | 8/2006 | van Zoest | H04L 29/06027 725/134 |
| 2007/0092149 A1 | 4/2007 | Sung | |
| 2011/0246673 A1* | 10/2011 | Kishore | H04L 65/602 709/247 |

OTHER PUBLICATIONS

AGFA HealthCare, color brochure "IMPAX 6: Digital Image and Information Management," © 2012 Agfa HealthCare N.V. Downloaded from http://www.agfahealthcare.com/global/en/he/library/libraryopen?ID=32882925. Accessed on Feb. 9, 2015.

AGFA HealthCare, IMPAX 6.5 Datasheet (US)2012. © 2012 Agfa HealthCare N.V. Downloaded from http://www.agfahealthcare.com/global/en/he/library/libraryopen?ID=37459801, Accessed on Feb. 9, 2015.

AMD Technologies, Inc., Catella PACS 5.0 Viewer User Manual (112 pgs), © 2010, AMD Technologies, Inc. (Doc. 340-3-503 Rev. 01). Downloaded from http://www.amdtechnologies.com/lit/cat5viewer.pdf. Accessed on Feb. 9, 2015.

ASPYRA's Imaging Solutions, 3 page color print out. Accessed at http://www.aspyra.com/imaging-solutions. Accessed on Feb. 9, 2015.

(Continued)

*Primary Examiner* — Soo Park
(74) *Attorney, Agent, or Firm* — Knobbe, Martens, Olson & Bear LLP

(57) ABSTRACT

Systems and methods for ensuring that images are compressed in a format that may be decompressed at a speed that is acceptable to a particular user and/or viewing environment are disclosed herein.

21 Claims, 8 Drawing Sheets

(56) References Cited

OTHER PUBLICATIONS

AVREO, interWorks—RIS/PACS package, 2 page color brochure, © 2014, Avreo, Inc. (Document MR-5032 Rev. 4). Downloaded from http://www.avreo.com/ProductBrochures/MR-5032Rev.%204interWORKS%20RISPACSPackage.pdf. Accessed on Feb. 9, 2015.
BRIT Systems, BRIT PACS View Viewer, 2 page color brochure, (BPB-BPV-0001). Downloaded from http://www.brit.com/pdfs/britpacsview.pdf. Accessed on Feb. 9, 2015.
BRIT Systems, Roentgen Works—100% Browers-based VNA (Vendor Neutral Archive/PACS), © 2010 BRIT Systems, 1 page color sheet. Accessed at http://www.roentgenworks.com/PACS. Accessed on Feb. 9, 2015.
BRIT Systems, Vision Multi-modality Viewer—with 3D, 2 page color brochure, (BPB-BVV-0001 REVC). Downloaded from http://www.brit.com/pdfs/BPB-BVV-0001REVC_BRIT_Vision_Viewer.pdf. Accessed on Feb. 9, 2015.
CANDELiS, ImageGrid™: Image Management Appliance, 6 page color brochure. (AD-012 Rev. F Nov. 2012), © 2012 Candelis, Inc. Downloaded from http://www.candelis.com/images/pdf/Candelis_ImageGrid_Appliance_20111121.pdf. Accessed on Feb. 9, 2015.
Carestream, Cardiology PACS, 8 page color brochure. (CAT 866 6075 06/12). © Carestream Health, Inc., 2012. Downloaded from http://www.carestream.com/cardioPACS_brochure_M1-877.pdf. Accessed on Feb. 9, 2015.
Carestream, Vue PACS, 8 page color brochure. (CAT 300 1035 05/14). © Carestream Health, Inc., 2014. Downloaded from http://www.carestream.com/csPACS_brochure_M1-876.pdf. Accessed on Feb. 9, 2015.
Cerner, Radiology—Streamline image management, 2 page color brochure, (fl03_332_10_v3). Downloaded from http://www.cerner.com/uploadedFiles/Clinical_Imaging.pdf. Accessed on Feb. 9, 2015.
CoActiv, EXAM-PACS, 2 page color brochure, © 2014 CoActiv, LLC. Downloaded from http://coactiv.com/wp-content/uploads/2013/08/EXAM-PACS-BROCHURE-final-web.pdf. Accessed on Feb. 9, 2015.
DR Systems, Dominator™ Guide for Reading Physicians, Release 8.2, 546 pages, (TCP-000260-A), © 1997-2009, DR Systems, Inc. Downloaded from http://resources.dominator.com/assets/004/6999.pdf. Document accessed Feb. 9, 2015.
DR Systems, DR Scheduler User Guide, Release 8.2, 410 pages, (TCP-000115-A), © 1997-2009, DR Systems, Inc. Downloaded from https://resources.dominator.com/assets/003/6850.pdf. Document accessed Feb. 9, 2015.
Fujifilm Medical Systems, SYNAPSE® Product Data, Synapse Release Version 3.2.1, Foundation Technologies, 4 page color brochure, (XBUSSY084) Aug. 2008. Downloaded from http://www.fujifilmusa.com/shared/bin/foundation.pdf. Accessed on Feb. 9, 2015.
Fujifilm Medical Systems, SYNAPSE® Product Data, Synapse Release Version 3.2.1, Server Modules and Interfaces, 4 page color brochure, (XBUSSY085) Aug. 2008. Downloaded from http://www.fujifilmusa.com/shared/bin/server-interface.pdf. Accessed on Feb. 9, 2015.
Fujifilm Medical Systems, SYNAPSE® Product Data, Synapse Release Version 3.2.1, Workstation Software, 4 page color brochure, (XBUSSY082) Aug. 2008. Downloaded from http://www.fujifilmusa.com/shared/bin/workstation.pdf. Accessed on Feb. 9, 2015.
GE Healthcare, Centricity PACS, in 8 page printout. Accessed at http://www3.gehealthcare.com/en/products/categories/healthcare_it/medical_imaging_informatics - ris-pacs-cvis/centricity_pacs. Accessed on Feb. 9, 2015.
Handylife.com—Overview of Handy Patients Enterprise, in 2 page printout. Accessed from http://www.handylife.com/en/software/overview.html. Accessed on Feb. 18, 2015.
Handylife.com—Features of Handy Patients Enterprise, in 4 page printout. Accessed from http://www.handylife.com/en/software/features.html. Accessed on Feb. 18, 2015.
Handylife.com—Screenshots of Handy Patients Enterprise, in 2 page printout. Accessed from http://www.handylife.com/en/software/screenshots.html. Accessed on Feb. 18, 2015.
iCRco, I See The Future, in 12 pages, color brochure, (BR080809AUS), © 2009 iCRco.ClarityPACS. Downloaded from http://www.claritypacs.com/pdfs/ISeeFuture_26_Web.pdf. Accessed on Feb. 9, 2015.
Imageanalysis, dynamika, 2 page color brochure. Downloaded from http://www.imageanalysis.org.uk/what-we-do. Accessed on Feb. 9, 2015.
Imageanalysis, MRI Software, in 5 page printout. Accessed at http://www.imageanalysis.org.uk/mri-software. Accessed on Feb. 9, 2015.
IMSI, Integrated Modular Systems, Inc., Hosted / Cloud PACS in one page printout. Accessed at http://www.imsimed.com/#!products-services/ctnu. Accessed on Feb. 9, 2015.
Infinitt, PACS, RIS, Mammo PACS, Cardiology Suite and 3D/Advanced Visualization | Infinittna, 2 page printout. Accessed at http://www.infinittna.com/products/radiology/radiology-pacs. Accessed on Feb. 9, 2015.
Intelerad, IntelePACS, 2 page color brochure, © 2014 Intelerad Medical Systems Incoprorated. Downloaded http://www.intelerad.com/wp-content/uploads/sites/2/2014/08/IntelePACS-brochure.pdf. Accessed on Feb. 9, 2015.
Intelerad, InteleViewer, 2 page color brochure, © 2014 Intelerad Medical Systems Incoprorated. Downloaded from http://www.intelerad.com/wp-content/uploads/sites/2/2014/09/InteleViewer-brochure.pdf. Accessed on Feb. 9, 2015.
Intuitive Imaging Informatics, ImageQube, 1 page in color. Downloaded from http://www.intuitiveimaging.com/2013/pdf/ImageQube%20one-sheet.pdf. Accessed on Feb. 9, 2015.
Kuhl, Helen: Comparison Chart/PACS, Customers Are Happy, But Looking for More, (color) Imaging Techology News, itnonline.com, May 2012, pp. 24-27. Downloaded from http://www.merge.com/MergeHealthcare/media/company/In%20-The%20News/merge-pacs-comparison.pdf. Accessed on Feb. 9, 2015.
LUMEDX CardioPACS 5.0 Web Viewer, Cardiopacs Module, 2 page color brochure, (506-10011 Rev A). Downloaded from http://cdn.medicexchange.com/images/whitepaper/cardiopacs_web_viewer.pdf?1295436926. Accessed on Feb. 9, 2015.
LUMEDX Cardiovascular Information System, CardioPACS, one page in color printout. Accessed at http://www.lumedx.com/pacs.aspx. Accessed on Feb. 9, 2015.
McKesson Enterprise Medical Imagining and PACS | McKesson, 1 page (color) printout. Accessed at http://www.mckesson.com/providers/health-systems/diagnostic-imaging/enterprise-medical-imaging. Accessed on Feb. 9, 2015.
Medweb Radiology Workflow Solutions, Radiology Workflow Solutions, Complete Workflow & Flexible Turnkey Solutions, Web RIS/PACS with Advanced Viewer, 3 page color brochure, © 2006-2014 Medweb. Downloaded from http://www.medweb.com/docs/rispacs_brochure_2014.pdf. Accessed on Feb. 9, 2015.
Merge Radiology Solutions, Merge PACS, A real-time picture archiving communication system, (PAX-21990 rev 2.0), 2 page color brochure. Downloaded from http://www.merge.com/MergeHealthcare/media/documents/brochures/Merge_PACS_web.pdf. Accessed on Feb. 9, 2015.
NOVARAD Enterprise Imaging Solutions, NOVAPACS, 2 page (color) printout. Accessed at http://ww1.novarad.net/novapacs. Accessed on Feb. 9, 2015.
PACSPLUS, PACSPLUS Server, 1 page (color) printout. Accessed at http://www.pacsplus.com/01_products/products_01.html. Accessed on Feb. 9, 2015.
PACSPLUS, PACSPLUS Workstation, 3 page (color) printout. Accessed at http://www.pacsplus.com/01_products/products_01_html. Accessed on Feb. 9, 2015.
Philips IntelliSpace PACS, in 2 color page printout. Accessed at https://www.healthcare.philips.com/main/products/healthcare_informatics/products/enterprise_imaging_informatics/isite_pacs. Accessed on Feb. 9, 2015.

(56) References Cited

OTHER PUBLICATIONS

Philips, IntelliSpace: Multi-modality tumor tracking application versus manual PACS methods, A time study for Response Evaluation Criteria in Solid Tumors (RECIST). 2012, Koninklijke Philips Electronics N.V., in four pages.

RamSoft, RIS PACS Teleradiology, PowerServer PACS, Lite PACS, XU PACS Compare RamSoft PACS Products, 2 color page printout. Accessed at http://www.ramsoft.com/products/powerserver-pacs-overview. Accessed on Feb. 9, 2015.

Sage Intergy PACS | Product Summary. Enhancing Your Workflow by Delivering Web-based Diagnostic Images When and Where You Need Them, in 2 color pages. (IRV-SS-INTPACS-PSS-031309). © 2009 Sage Software Healcare, Inc. Downloaded from http://www.greenwayhealth.com/solutions/intergy/. Accessed on Feb. 9, 2015.

ScImage, Cardiology PACS, in 8 color page printout. Accessed at http://www.scimage.com/solutions/clinical-solutions/cardiology. Accessed on Feb. 9, 2015.

Sectra RIS PACS, in 2 color page printout. Accessed at https://www.sectra.com/medical/diagnostic_imaging/solutions/ris-pacs/. Accessed on Feb. 9, 2015.

Siemens syngo.plaza, Features and Benefits, in 2 color page printout. Accessed at http://www.healthcare.siemens.com/medical-imaging-it/imaging-it-radiology-image-management-pacs/syngoplaza/features. Accessed on Feb. 9, 2015.

Simms | RIS and PACS Medical Imaging Software, in 2 color page printout. http://www.mysimms.com/ris.pacs.php. Accessed on Feb. 9, 2015.

Stryker, Imaging—OfficePACS Power Digital Imaging, in one color page printout. Accessed from http://www.stryker.com/emea/Solutions/Imaging/OfficePACSPowerDigitalImaging/index.htm. Accessed on Feb. 9, 2015.

Stryker, OfficePACS Power—Digital Imaging, 8 page color brochure, (MPP-022 Rev 4 BC/MP 300 1/07). © 2007 Stryker. Downloaded from http://www.stryker.com/emea/Solutions/imaging/OfficePACSPowerDigitalImaging/ssLINK/emea/1557/022268. Accessed on Feb. 9, 2015.

UltraRAD—ultra VISION, 1 page (color). Downloaded from http://www.ultraradcorp.com/pdf/UltraVISION.pdf. Accessed on Feb. 9, 2015.

VioStream for VitreaView, 2 color pages printout. Accessed at http://www.vitalimages.com/solutions/universal-viewing/viostream-for-vitreaview. Accessed on Feb. 9, 2015.

Visage Imaging Visage 7, 3 color page printout. Accessed at http://www.visageimaging.com/visage-7. Accessed on Feb. 9, 2015.

VIZTEK Radiology PACS Software Vixtek Opal-RAD, 4 color page printout. Accessed at http://viztek.net/products/opal-rad. Accessed on Feb. 9, 2015.

Voyager Imaging—Voyager PACS Radiologist Workstation, 2 page color brochure. Downloaded from http://www.intellirad.com.au/assets/Uploads/Voyager-PacsWorkstations.pdf?. Accessed on Feb. 9, 2015.

Voyager Imaging—Voyager PACS, 3 page color brochure. Downloaded from http://www.intellirad.com.au/index.php/assets/Uploads/Voyager-Pacs3.pdf. Accessed on Feb. 9, 2015.

\* cited by examiner

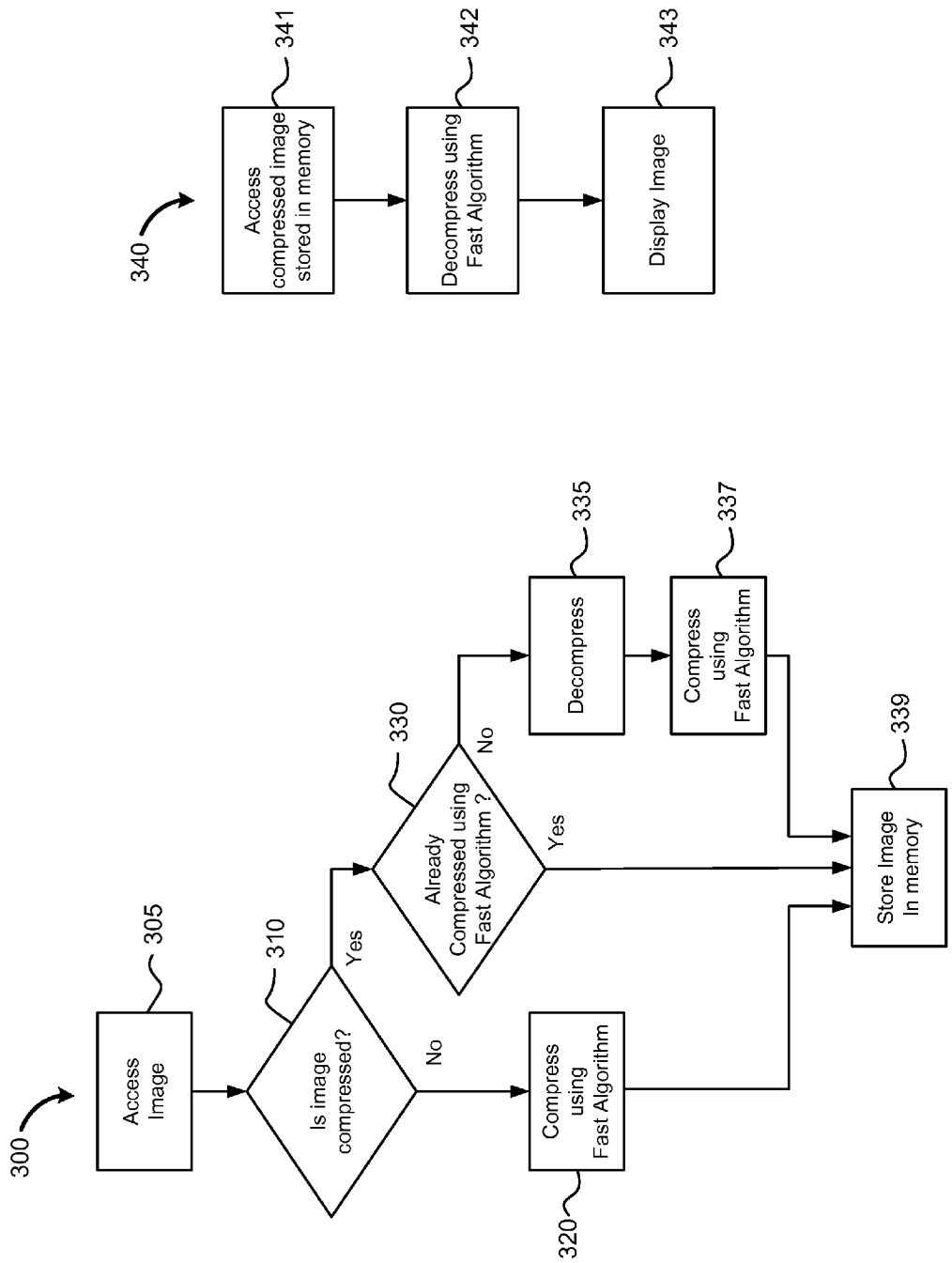

DUAL TECHNIQUE COMPRESSION

CROSS-REFERENCE TO RELATED APPLICATIONS

This application is a continuation of U.S. patent application Ser. No. 13/359,363, filed Jan. 26, 2012, and titled "DUAL TECHNIQUE COMPRESSION," which claims the benefit of priority under 35 U.S.C. §119(e) of U.S. Provisional Application No. 61/437,236, filed Jan. 28, 2011, each of which is hereby incorporated by reference herein in its entirety.

BACKGROUND

Medical imaging exams can be acquired by a number of different medical imaging techniques, including computed tomography (CT), magnetic resonance imaging (MRI), ultrasound, nuclear medicine, positron emission computed tomography (PET), digital angiography, mammography, computed radiography, digital radiography, fluoroscopy, and others.

Medical imaging exams often consist of a large amount of digital data, some consisting of thousands of images. Interpretation of these large medical imaging exams by doctors can be inefficient due to transmission and computer bottlenecks that slow image transmission and display. There is a need for new ways of managing medical imaging exams that increase physician efficiency.

SUMMARY

For purposes of this summary, certain aspects, advantages, and novel features are described herein. It is to be understood that not necessarily all such advantages may be achieved in accordance with any particular embodiment. Thus, for example, those skilled in the art will recognize that the invention may be embodied or carried out in a manner that achieves one advantage or group of advantages as taught herein without necessarily achieving other advantages as may be taught or suggested herein.

Embodiments of methods and system described herein can be used to increase the performance of image interaction by increasing the number of images that can be stored in memory for rapid access without requiring an increase in physical memory or change in memory available to the program. A feature of the systems and methods described herein is the use of compression/decompression technology that is fast and that may be different than the compression algorithm used to store the transmitted images.

In one embodiment, a method of preparing images for use by a computing device comprising one or more hardware processors comprises receiving, at the computing device, a compressed image comprising data generated by compressing an image file using a first compression technique and determining whether the first compression technique provides at least a threshold decompression speed. In response to determining that the first compression technique does not provide at least the threshold decompression speed, decompressing the compressed image, recompressing the decompressed image using a second compression technique that does provide at least the threshold decompression speed, and storing the recompressed image in a memory so that the decompressed image is available for decompression on the computing device or another computing device. In response to determining that the first compression technique does provide at least the threshold decompression speed, storing the compressed image in the memory so that the compressed image is available for decompression on the computing device or another computing device.

BRIEF DESCRIPTION OF THE DRAWINGS

FIG. 6 is a flowchart illustrating one embodiment of a method of compressing images using a fast algorithm.

FIG. 7 is a flowchart illustrating one embodiment of a method of decompressing and displaying images that have been compressed.

Figure 1:
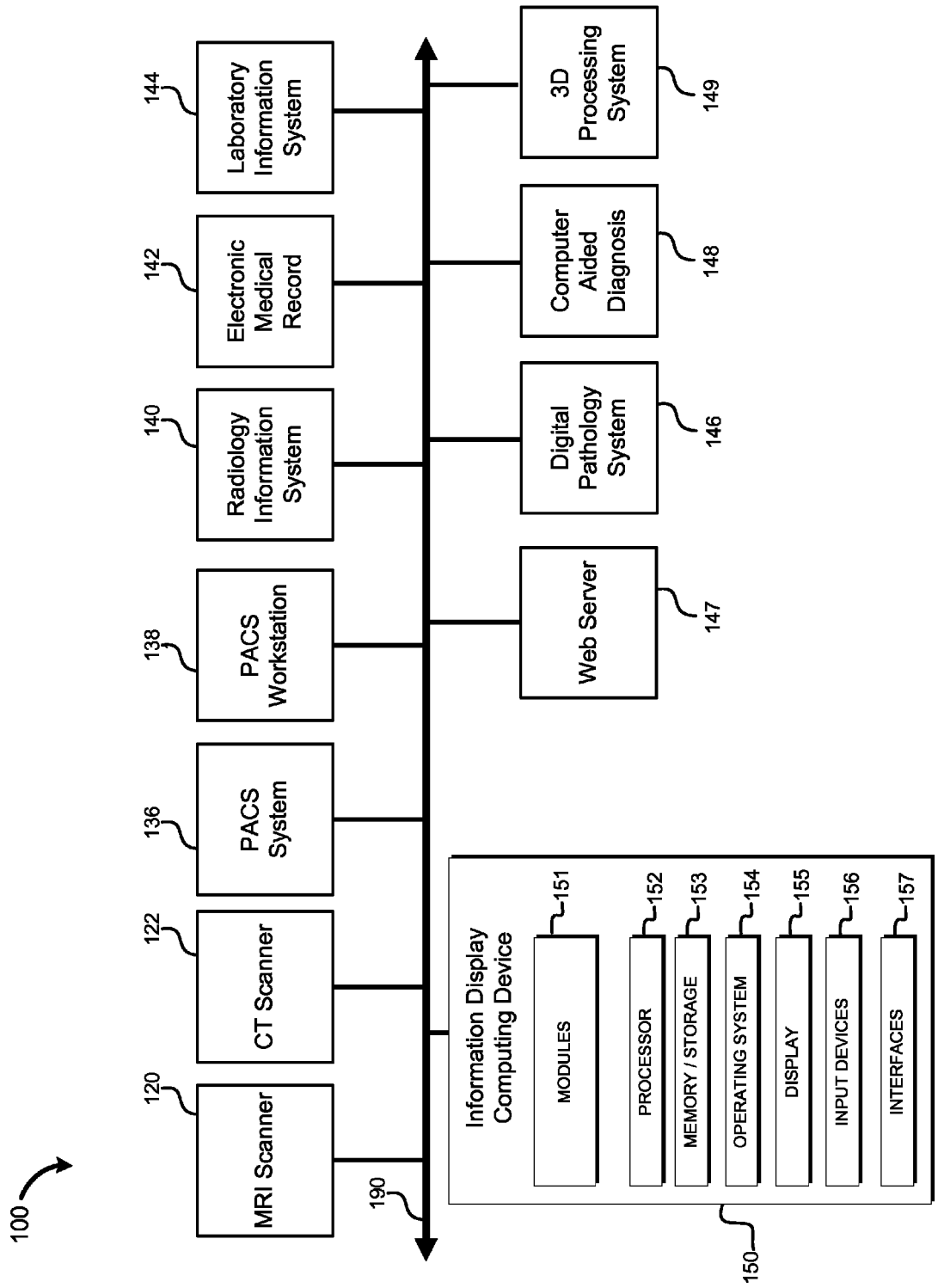
FIG. 1 is a block diagram illustrating one embodiment of a computing system that may be used to implement certain systems and methods described herein.

These and other features will now be described with reference to the drawings summarized above. The drawings and the associated descriptions are provided to illustrate certain embodiments of the invention and not to limit the scope of the invention. Throughout the drawings, reference numbers may be re-used to indicate correspondence between referenced elements.

DETAILED DESCRIPTION

Embodiments of the disclosure will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the disclosure. Furthermore, embodiments of the disclosure may include several novel features, no single one of which is solely responsible for its desirable attributes or which is essential to practicing the embodiments of the disclosure herein described.

As used herein, the terms "viewer" and "user" are used interchangeably to describe an individual (or group of individuals) that interfaces with a computing device. Users may include, for example, doctors, radiologists, hospital staff, or other individuals involved in acquisition, analysis, storage, management, or other tasks related to medical images. Any discussion herein of user preferences should be construed to also, or alternatively, include user group preferences, site preferences, system preferences, and/or default software preferences.

Depending on the embodiment, the methods described with reference to the flowcharts, as well as any other methods discussed herein, may include fewer or additional blocks and/or the blocks may be performed in a different order than is illustrated. Software code configured for execution on a computing device in order to perform the methods may be provided on a computer readable medium, such as a compact disc, digital video disc, flash drive, hard drive, memory device or any other tangible medium. Such software code may be stored, partially or fully, on a memory of a computing device (e.g., RAM, ROM, etc.), such as the computing system 150 (see discussion of FIG. 1, below), and/or other computing devices illustrated in the figures, in order to perform the respective methods. For ease of explanation, the methods will be described herein as performed by the computing system 150, but the methods are not limited to performance by the computing system 150 and should be interpreted to include performance by any one or more of the computing devices noted herein and/or any other suitable computing device.

Radiologists and other doctors often view very large medical images (in raw data size and/or number of pixels) from which important information regarding a past, current, and/or potential future condition of the subject (e.g. a patient) can be determined. The speed at which these images are available for viewing by the doctor may greatly impact the time required to properly assess a medical image or image series comprising multiple medical images.

For purposes of illustration and ease of understanding, medical imaging information (e.g., medical images and images series) is discussed throughout this specification. However, the systems and methods discussed herein may be used for other types of image data as well as non-imaging digital information stored in a computing device's memory. In addition, the systems and methods described herein could be used in a wide range of computing devices including personal computers, PDA's, tablets, and cell phones such as the iPhone.

Efficiency of interpreting images may be increased if images of an exam are quickly available (e.g., after selection of an exam for viewing) and/or navigation from image to image is rapid. The need for rapid access to images may enhance many functions including, for example:

Radiologists and other physicians can more quickly interpret medical exams by more rapidly navigating through the images within an exam, often repeatedly viewing images within an exam.

Speed of real-time comparison of images or cross referencing of images within a study, e.g., with a 3D cursor, may be increased. For example, speed of comparing images may be increased in the example case where a user needs to view a spatial position corresponding to an anatomic position within the patient that may be imaged multiple times within an exam, for example Images obtained in different anatomic planes, e.g., axial, sagittal, and coronal planes.

Images obtained with different imaging techniques, e.g. in MRI, T1, T2, diffusion, etc.

Images within an exam obtained before and after contrast administration.

Images obtained at different times, e.g. a dynamic enhanced study.

Simultaneous comparison of images from different exams may be performed more rapidly. For example, a radiologist may wish to view a series of axial images through the lungs and simultaneously view a set of similar images obtained 6 months earlier to assess for changes that may have occurred.

Simultaneous comparison of images from different modalities where imaging was obtained at different or substantially the same time, e.g., PET CT and PET MRI, may be performed more rapidly.

Derived images, e.g., maximum intensity projection (MIP), multiplanar reformatting (MPR), and 3D volume or surface rendering, may be created on-the-fly more rapidly.

Computer Aided Diagnosis (CAD) and post-processing techniques, wherein computer algorithms analyze or otherwise process images, may be performed more rapidly.

Medical imaging exams may be stored on a computer server and transferred to the computing device used by the doctor to view the exam, for example, using a LAN, WAN, the Internet, or physical media such as a CD, DVD, or flash memory device. The computing device used by the doctor could be a personal computer, PDA, or cell phone, for example, such as any of the one or more devices or configurations of devices discussed with reference to the information display computing device 150 illustrated in FIG. 1.

Often the speed of transfer via a network or from physical media is too slow for sufficiently rapid display of images in a medical imaging exam. For example, radiologists may desire to view a series of 2 megabyte images at a rate of 15 images/second to accurately interpret the exam. Since transmission of the images from a central server may be too slow to support that speed, images may be transmitted and stored in local fast computer memory (e.g., RAM, flash memory, etc.) prior to viewing by the user.

Therefore, images are often transferred into the memory of the computing device in advance of the doctor navigating through the images. This may provide several advantages, such as one or more of:

With images stored in memory, they can be more rapidly displayed on demand.

During the course of viewing an exam, users often view each images multiple times. Storing the images in memory decreases the need to repeatedly retrieve the images from the server, decreasing server and network utilization.

Images can be preloaded into memory in advance of the radiologist needing them.

When a doctor opens an exam, he might spend a few seconds reading clinical or other data, during which time images can be loaded into memory.

While he is looking at images, other images in the exam can be retrieved and stored in memory In the case where the workstation can predict the next exam to be read, for example through rules that prioritize exam reading or a worklist, exams that the radiologist is likely to view can be loaded in the local memory in advance.

While loading images into memory may have one or more advantages, the available memory in various computing devices may be insufficient for a number of reasons, including:

Limited physical memory.

Operating System limitations that restrict the addressable memory.

Limited memory available to the program displaying the images, for example because of limitations in the software model, e.g. browser, or usage of memory by other programs or processes.

One potential solution to increasing the number of images stored in memory is to store them in compressed format in memory. In fact, medical images are often transmitted in a compressed format to a viewing computing device. However, use of compressed images introduces other potential inefficiencies for a computing system. For example, decompression of images may be too slow to allow sufficiently rapid decompression and display of the images. For example, a radiologist may require that images be displayed at a rate of 20 images/second, corresponding to a new image every 50 msec. If the in-memory decompression speed is 100 msec/image, images could only be decompressed at half the required rate.

In fact, some forms of compression used in medical imaging have relatively long decompression times, such as JPEG 2000. In those cases, image decompression speed and, therefore, image display speed may be unacceptably slow, despite the fact that the images are stored in fast memory. While it may be possible to decompress the images and store them in uncompressed format in memory, insufficient memory may be available to store the desired number of uncompressed images in memory.

One feature of many of the systems and methods described herein is the use of a second compression algorithm that is faster than the compression algorithm used on received compressed images. For example, images received by a computing device may be compressed using an algorithm that requires 250 msec/image for decompression. Prior to image viewing by the user, these images might be decompressed and then recompressed with a fast compression algorithm that might require only 10 msec/image for decompression. This would result in much faster image viewing for the user and allow more images to be stored in memory compared to storing the images in memory without compression.

Image compression may be utilized within PACS to decrease the storage requirements for medical imaging exams as well as to increase transmission speeds across networks. A variety of compression techniques may be used, including, for example, DICOM JPEG lossy compression, DICOM JPEG lossless compression, DICOM JPEG 2000 lossy compression, DICOM JPEG 2000 lossless compression, and the like. Image compression could be performed in a number of places and by a number of different devices, including, for example, by a medical scanner prior to being transferred (e.g., to a PACS), by a computer system interfaced to the medical scanner that receives images from the medical scanner, compresses them, and then transfers the compressed images, by the PACS itself, for example on receipt of images or at the time images are stored in a long term archive, and/or many other devices. With reference to FIG. 1, for example, compressed or uncompressed images stored in a PACS System 136 may be compressed prior to transfer via network 190 to computing device 150 (or simply "computing device 150") for display. This might be performed to increase transfer speed in cases where transmission times would otherwise be longer than desired. For example, images transferred from PACS System 136 to computing device 150 via network 190 might be compressed. This might significantly speed transmission, for example when network 190 comprises the Internet or a relatively slow cellular data transmission network, for example.

Embodiments of systems and methods described herein may first decompress images that were compressed using a slow compression/decompression algorithm and then employ a second compression algorithm that supports very rapid decompression. This process of decompression followed by recompression may occur prior to the user accessing the images, for example in a background operation while the user is performing another task. In some embodiments, the process of decompression followed by recompression may occur prior to or after transmission of the images to the computing device.

The compression technique used for recompression and decompression for viewing on the computing device might be one that is inherently efficient, could be chosen based on performance characteristics of the particular computing device, characteristics of the particular image, or other related characteristics. For example, a decompression algorithm might be very fast on a particular computing device because of the hardware acceleration within the CPU or a GPU that can be leveraged for a particular decompression algorithm, while a different decompression algorithm might be fastest on another computing device having different characteristics.

Example Computing Systems

FIG. 1 is a system diagram which shows the various components of a system 100 for displaying information utilizing certain systems and methods described herein. As shown, the system 100 may include an information display computing device 150 (also referred to herein as a "computing device 150") and may include other systems, including those shown in FIG. 1.

The information display computing device 150 may take various forms. In one embodiment, the information display computing device 150 may be a computer workstation having information display modules 151. In other embodiments, modules 151 may reside on another computing device, such as a web server, and the user directly interacts with a second computing device that is connected to the web server via a computer network. The modules 151 will be described in detail below.

In one embodiment, the information display computing device 150 comprises a server, a desktop computer, a workstation, a PACS workstation, a laptop computer, a mobile computer, a smartphone, a tablet computer, a cell phone, a personal digital assistant, a gaming system, a kiosk, an audio player, any other device that utilizes a graphical user interface, including office equipment, automobiles, airplane cockpits, household appliances, automated teller machines, self-service checkouts at stores, information and other kiosks, ticketing kiosks, vending machines, industrial equipment, and/or a television, for example.

The information display computing device 150 may run an off-the-shelf operating system 154 such as a Windows, Linux, MacOS, Android, or iOS. The information display computing device 150 may also run a more specialized operating system which may be designed for the specific tasks performed by the computing device 150.

The information display computing device 150 may include one or more computing processors 152. The computer processors 152 may include central processing units (CPUs), and may further include dedicated processors such as graphics processor chips, or other specialized processors. The processors generally are used to execute computer instructions based on the information display software modules 151 to cause the computing device to perform operations as specified by the modules 151. The modules 151 may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. For example, modules may include software code written in a programming language, such as, for example, Java, JavaScript, ActionScript, Visual Basic, HTML, C, C++, or C#. While "modules" are generally discussed herein with reference to software, any modules may alternatively be represented in hardware or firmware. Generally, the modules described herein refer to logical modules that may be combined with other modules or divided into sub-modules despite their physical organization or storage.

The information display computing device 150 may also include memory 153. The memory 153 may include volatile data storage such as RAM or SDRAM. The memory 153 may also include more permanent forms of storage such as a hard disk drive, a flash disk, flash memory, a solid state drive, or some other type of non-volatile storage.

The information display computing device 150 may also include or be interfaced to one or more display devices 155 that provide information to the users. Display devices 155 may include a video display, such as one or more high-resolution computer monitors, or a display device integrated into or attached to a laptop computer, handheld computer, smartphone, computer tablet device, or medical scanner. In other embodiments, the display device 155 may include an LCD, OLED, or other thin screen display surface, a monitor, television, projector, a display integrated into wearable glasses, or any other device that visually depicts user interfaces and data to viewers.

The information display computing device 150 may also include or be interfaced to one or more input devices 156 which receive input from users, such as a keyboard, trackball, mouse, 3D mouse, drawing tablet, joystick, game controller, touch screen (e.g., capacitive or resistive touch screen), touchpad, accelerometer, video camera and/or microphone.

The information display computing device 150 may also include one or more interfaces 157 which allow information exchange between information display computing device 150 and other computers and input/output devices using systems such as Ethernet, Wi-Fi, Bluetooth, as well as other wired and wireless data communications techniques.

The modules of the information display computing device 150 may be connected using a standard based bus system. In different embodiments, the standard based bus system could be Peripheral Component Interconnect ("PCI"), PCI Express, Accelerated Graphics Port ("AGP"), Micro channel, Small Computer System Interface ("SCSI"), Industrial Standard Architecture ("ISA") and Extended ISA ("EISA") architectures, for example. In addition, the functionality provided for in the components and modules of information display computing device 150 may be combined into fewer components and modules or further separated into additional components and modules.

The information display computing device 150 may communicate and/or interface with other systems and/or devices. In one or more embodiments, the computing device 150 may be connected to a computer network 190. The computer network 190 may take various forms. It may include a wired network or a wireless network, or it may be some combination of both. The computer network 190 may be a single computer network, or it may be a combination or collection of different networks and network protocols. For example, the computer network 190 may include one or more local area networks (LAN), wide area networks (WAN), personal area networks (PAN), cellular or data networks, and/or the Internet.

Various devices and subsystems may be connected to the network 190. For example, one or more medical scanners may be connected, such as MRI scanners 120. The MRI scanner 120 may be used to acquire MRI images from patients, and may share the acquired images with other devices on the network 190. The network 190 may also include one or more CT scanners 122. The CT scanners 122 may also be used to acquire images and, like the MRI scanner 120, may then store those images and/or share those images with other devices via the network 190. Any other scanner or device capable of inputting or generating information that can be displayed as images or text could be included, including ultrasound, angiography, nuclear medicine, radiography, endoscopy, pathology, dermatology, etc.

Also connected to the network 190 may be a Picture Archiving and Communications System (PACS) 136 and PACS workstation 138.

The PACS System 136 may be used for the storage, retrieval, distribution and presentation of images (such as those created and/or generated by the MRI scanner 120 and CT Scanner 122). The medical images may be stored in an industry standard format, an open source format, a proprietary format, or some other format. One format for image storage in the PACS system is the Digital Imaging and Communications in Medicine (DICOM) format. The stored images may be transmitted digitally via the PACS system, often reducing or eliminating the need for manually creating, filing, or transporting film.

The network 190 may also be connected to a Radiology Information System (RIS) 140. The radiology information system 140 may be a computerized data storage system that is used by radiology departments to store, manipulate and distribute patient radiological information.

Also attached to the network 190 may be an Electronic Medical Record (EMR) system 142. The EMR system 142 may be configured to store and make accessible to a plurality of medical practitioners computerized medical records. Also attached to the network 190 may be a laboratory information system 144. Laboratory information system 144 may be a software system which stores information created or generated by clinical laboratories. Also attached to the network 190 may be a digital pathology system 146 used to digitally manage and store information related to medical pathology.

Also attached to the network 190 may be a computer aided diagnosis system (CAD) 148 used to analyze images. In one embodiment, the CAD functionality may reside in a computing device separate from the information display computing device 150 while in another embodiment the CAD functionality may reside within the information display computing device 150.

Also attached to the network 190 may be a 3D Processing System 149 used to perform computations on imaging information to create new views of the information, e.g., 3D volumetric display, Multiplanar Reconstruction (MPR) and Maximum Intensity Projection reconstruction (MIP). In one embodiment, the 3D processing functionality may reside in a computing device separate from the information display computing device 150 while in another embodiment the 3D processing functionality may reside within the information display computing device 150.

Also attached to network 190 may be web server 147 used to communicate information, for example via the internet or an intranet.

In other embodiments, other computing devices that store, provide, acquire, create and/or otherwise manipulate medical data may also be coupled to the network 190 and may be in communication with one or more of the devices illustrated in FIG. 1, such as with the information display computing device 150.

As will be discussed in detail below, the information display computing device 150 may be configured to interface with various networked computing devices in order to provide efficient and useful review of medical examination data that is stored among the various systems present in the network. In other embodiments, information display computing device 150 may be used to display non-medical information.

Depending on the embodiment, the other devices illustrated in FIG. 1 may include some or all of the same components discussed above with reference to the information display computing device 150.

Figure 2:
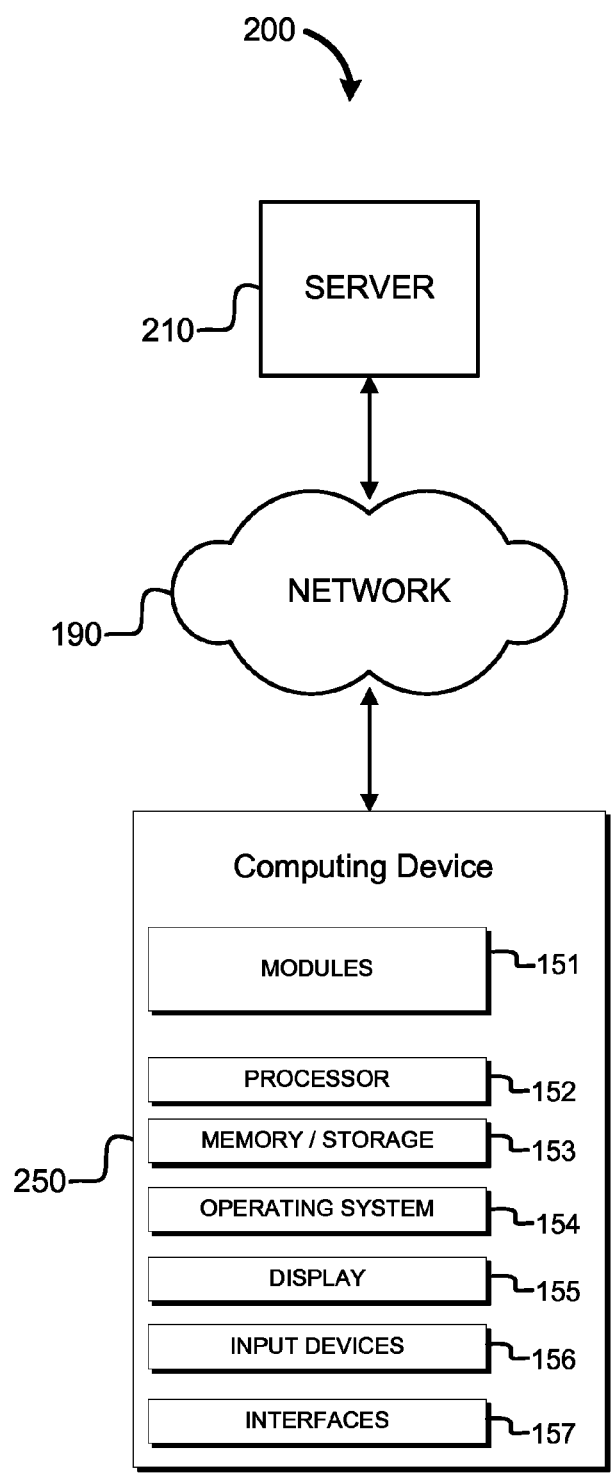
FIG. 2 is a block diagram illustrating one embodiment of a computing system that may be used to implement certain systems and methods described herein.

FIG. 2 is a block diagram which shows the various components of a system 200 for managing data utilizing certain systems and methods described herein. As shown, the system 200 may include a Computing Device 250 and may include other systems, including those shown in FIG. 2.

The computing device 250 may take various forms. In one embodiment, the computing device 250 may be a computer workstation having modules 151. In other embodiments, modules 151 may reside on another computing device, such as a web server, and the user directly interacts with a second computing device that is connected to the web server via a computer network. The modules 151 will be described in detail below.

Figure 9:
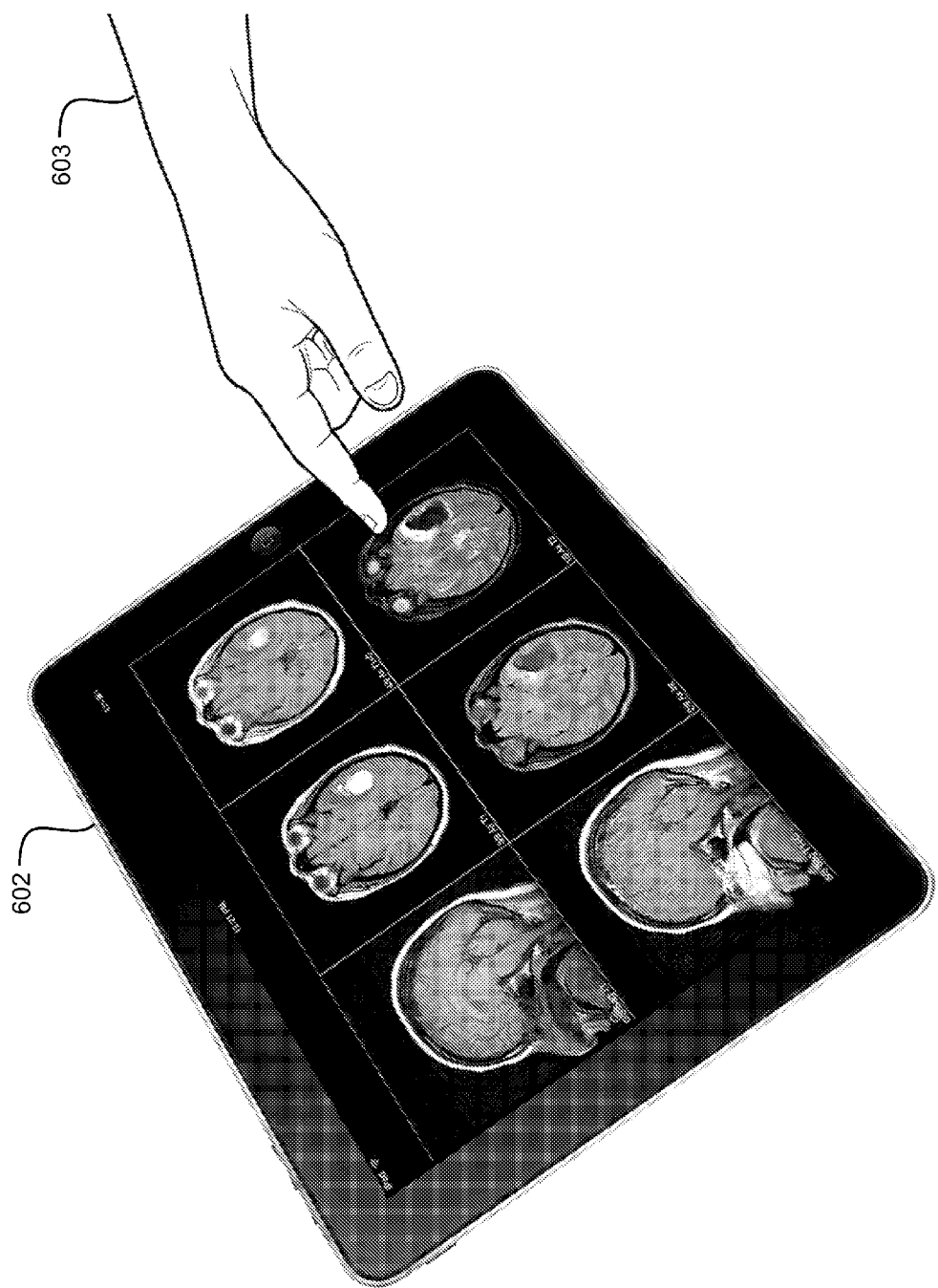
FIG. 9 is an example of a computing system that may be used to implement certain systems and methods described herein.

In one embodiment, the computing device 250 comprises a server, a desktop computer, a workstation, a laptop computer, a mobile computer, a Smartphone, a tablet computer (e.g., the tablet computer 602 of FIG. 9), a cell phone, a personal digital assistant, a gaming system, a kiosk, an audio player, any other device that utilizes a graphical user interface, including office equipment, automobiles, airplane cockpits, household appliances, automated teller machines, self-service checkouts at stores, information and other kiosks, ticketing kiosks, vending machines, industrial equipment, and/or a television, for example.

The computing device 250 may run an off-the-shelf operating system 154 such as a Windows, Linux, MacOS, Android, or iOS. The computing device 250 may also run a more specialized operating system which may be designed for the specific tasks performed by the computing device 250.

As with computing device 150 described herein with reference to FIG. 1, computing device 250 may include one more computing processors 152, may include memory storage 153, may include or be interfaced to one more display devices 155, may include or be interfaced to one or more input devices 156, and/or may include one or more interfaces 157.

Computing device 250 may communicate and/or interface with other systems and/or devices via network 190, in a similar or same manner as discussed with reference to computing device 150 in FIG. 1.

In FIG. 2, a Server 210 is in communication with the network 190 and, thus, with the computing device 250, which may allow, for example, communication of images or other data between server 210 and computing device 250.

Figure 3:
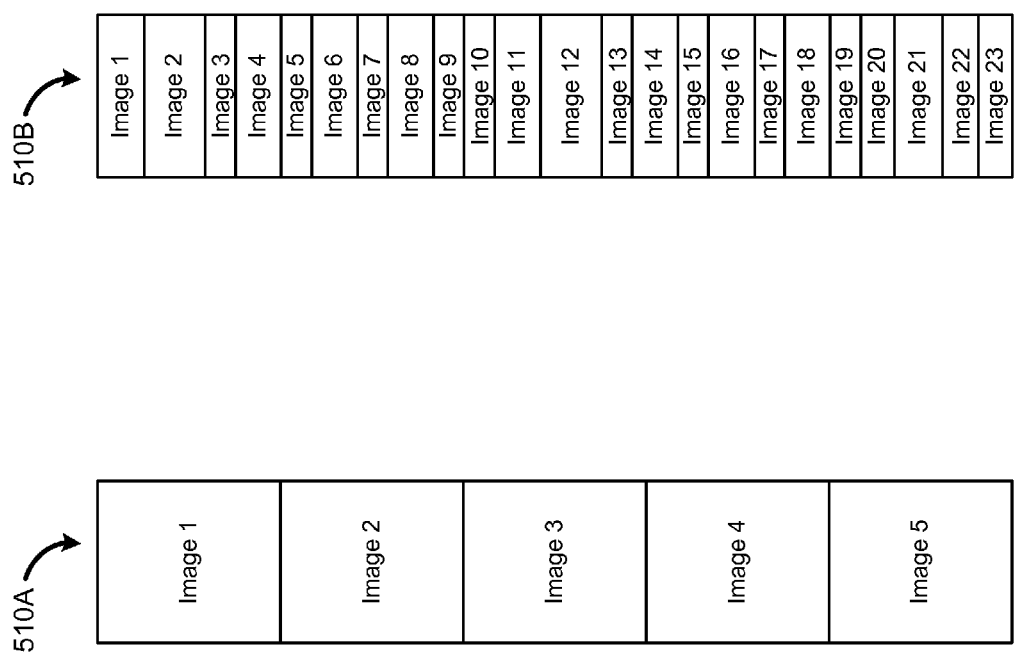
FIG. 3 is a block diagram illustrating one embodiment of a memory having two different types of image data stored therein.

FIG. 3 is a block diagram illustrating a memory 510 having two different types of image data stored therein. In particular, memory 510A illustrates the memory 510 filled with image data that is not compressed. In this example, only 5 images fit into the memory. Memory 510B illustrates the memory 510 filled with images that have been compressed. In this example, 23 compressed images are stored (510B) in the same space that only 5 uncompressed images fit (510A). Thus, with compression the 5 images stored uncompressed in memory 510A occupy substantially less memory, allowing an additional 18 images (for a total of 23 images) to be stored in the memory with the use of compression.

Figure 4:
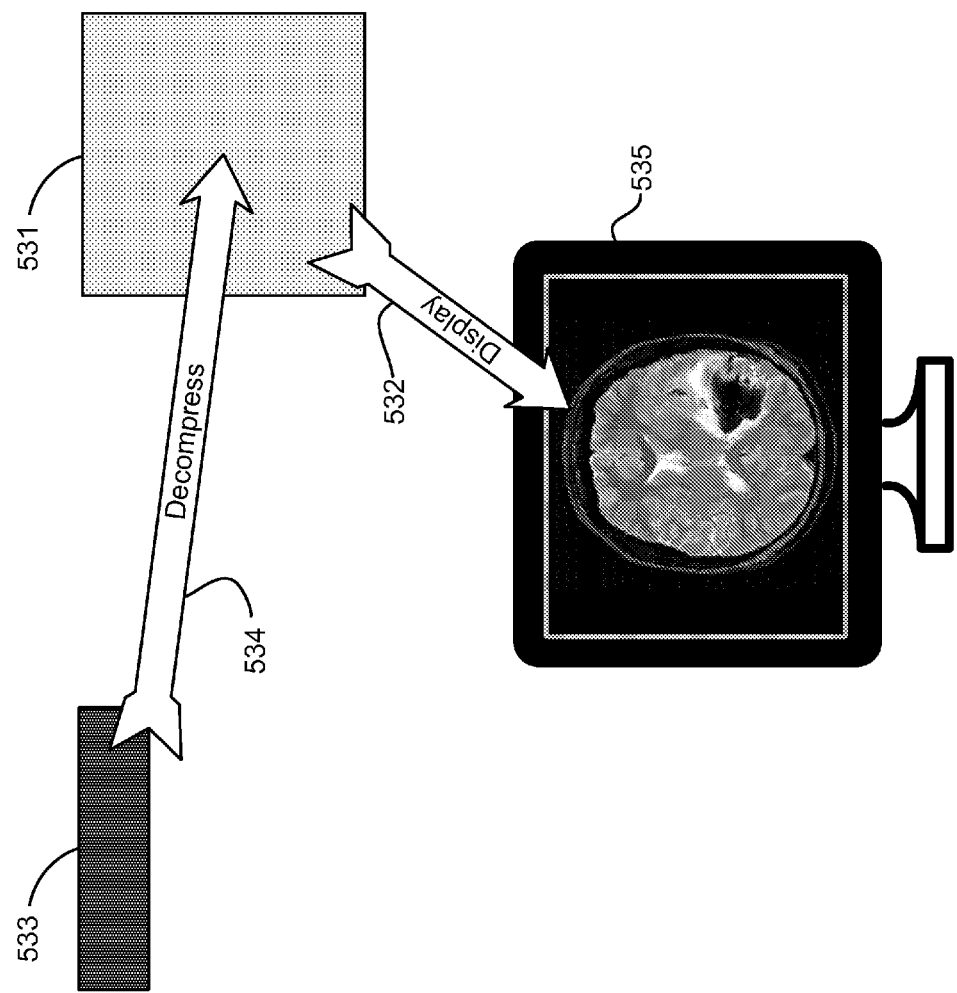
FIG. 4 is a block diagram illustrating one embodiment of a process of displaying images that have been stored in local memory in uncompressed format.

FIG. 4 is a block diagram illustrating a process of displaying images that have been stored in local memory in uncompressed format. In FIG. 4, a storage medium 533 (e.g., memory or mass storage device on a server or local computing device) stores a compressed image. Arrow 534 represents a decompression process being performed on the compressed image in order to generate an uncompressed image that can be displayed. In the embodiment of FIG. 4, the uncompressed image is stored on a storage medium 531, which may be the same storage medium 533 (e.g., different portions of a hard drive or RAM), or may be a different storage medium. For example the storage medium 533 may be a hard drive, while the storage medium 531 may be RAM of the computing device. With the images stored in uncompressed format, the process of display 532 would generally be very fast and involve transfer of the image data from the memory used for data storage to the display memory buffer of the device, with or without additional processing, e.g., magnification and/or alteration of grayscale and/or color mapping. However, if one of the images stored in compressed format on storage medium 533 is requested for display, the process of image display would require the additional step of image decompression prior to the image being available for display. Depending on the speed of decompression, this may not be practical as it may be too slow. For example, if decompression requires 250 msec per image that would limit image display speeds to 4 images/second.

Example Server Operations

Figure 5:
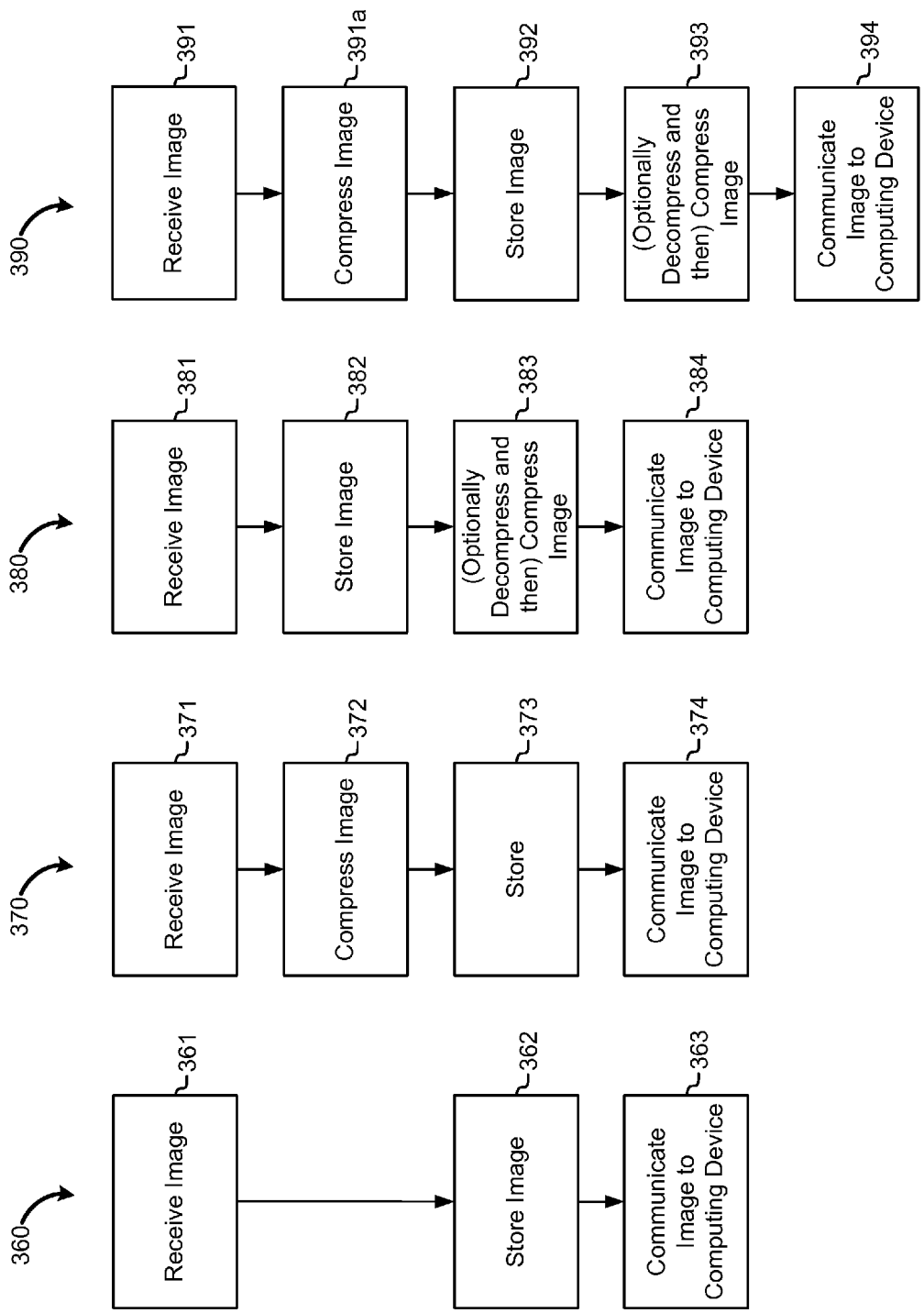
FIG. 5 includes flowcharts illustrating example methods that may occur on devices that communicate images to an information display computing device, such as the computing devices of FIG. 1 or 2.

Images or other data may be communicated to computing device 150 or computing device 250 from a variety of other devices as discussed herein, including but not limited to those depicted in FIG. 1 and FIG. 2. The flowcharts of FIG. 5 illustrate methods 360, 370, 380, and 390 that include sample activities that may occur on devices that communicate images to an information display computing device, e.g., computing device 150 or 250.

For purposes of illustration, these methods will be described as if they are performed on a PACS System in communication with the computing device 150, but this functionality could occur on the various other devices and systems described herein or any device or system that can communicate with computing device 150 or computing device 250, or could be performed by the computing device 150 or computing device 250.

Beginning with method 360, in block 361 an image is received by the PACS system, for example from a medical scanner or another device or system capable of communicating medical images. In block 362 the image is stored in the form it is received which could be compressed or uncompressed. In block 363, the image is communicated to the computing device 150.

Moving to method 370, in block 371 an image is received by the PACS system, for example from a medical scanner or another device or system capable of communicating medical images. In block 372 the image is compressed and in block 373 the compressed image is stored. In block 374, the compressed image is communicated to the computing device 150.

In method 380, at block 381 an image is received by the PACS system, for example from a medical scanner or another device or system capable of communicating medical images. In block 382 the image is stored in the form it is received which could be compressed or uncompressed. In block 383 the image is compressed prior to communication of the image to the computing device in block 384. Depending on whether the stored image is already compressed, the compression step in block 383 could be executed in several ways. In one embodiment, the compression step of block 383 would be skipped for images that were already compressed. In another embodiment, compressed images might be first decompressed and then recompressed in a different way. For example, images might be received in block 381 in compressed form using lossless compression. In block 383, images might be decompressed and then recompressed using lossy compression.

Method 390 includes blocks similar to those described in method 380, with blocks 391, 392, 393 and 394 corresponding to steps 381, 382, 383, and 384, respectively. However, in method 390, images are compressed at block 391*a* prior to storage in block 392. As shown in methods 380 and 390, all received images are compressed prior to transmission to the computing device 150. Additionally, in embodiments where the PACS system determines in block 383/393 whether an already compressed image is in a suitable format (e.g., whether the decompression algorithm running on the computing device 150 will be able to decompress the images in the desired time frame), images are all compressed in a format (e.g., using a compression algorithm that produces the desired format) that allows the images to be decompressed for viewing in a desired time frame. In one embodiment, this decompression and recompression allows the computing device 150 to more quickly view medical images received from the PACs server, since the computer device is not required to perform the decompression and compression itself, and because the images are already compressed in a preferred format that allows images to be quickly decompressed for viewing on the computing device 150.

Example Client Operations

Figure 8:
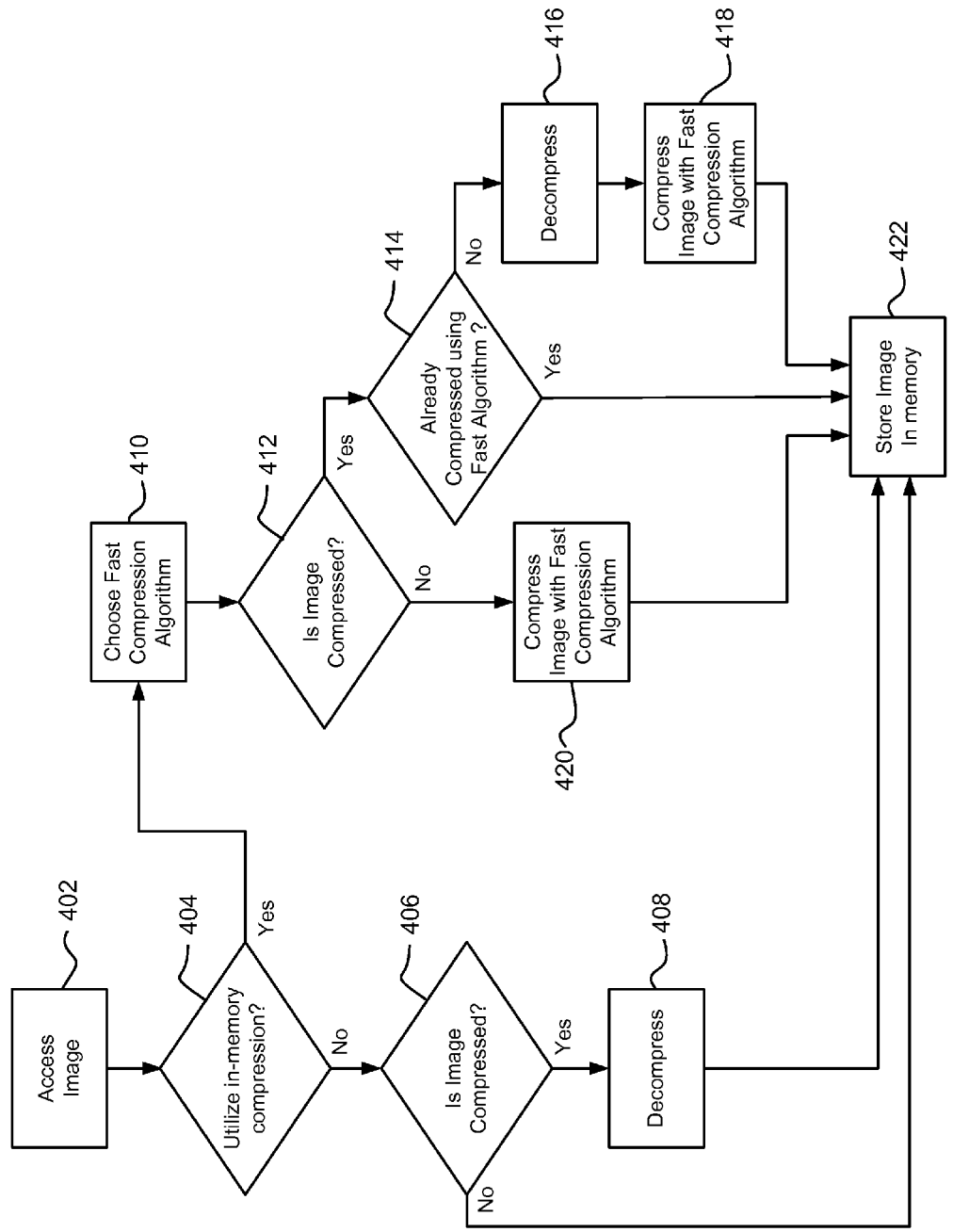
FIG. 8 is a flowchart illustrating one embodiment of a method of decompressing and recompressing images for rapid viewing of the images.

FIGS. 6, 7 and 8 are flowcharts illustrating example methods that may be performed by the computing device 150 of FIG. 1, or any other suitable computing device. For ease of explanation, the methods are described herein with reference to the computing device 150, with the understanding that in other embodiments the methods may be performed by any other suitable computing device. Depending on the embodiment, the flowcharts in the figures discussed may include additional or fewer blocks and/or the blocks may be performed in a different order than is illustrated.

For the purposes of illustrating the methods, two forms of compression will be considered, fast compression algorithms, referred to as "fast algorithms," and slower compression algorithms, referred to as "slow algorithms." An algorithm may be categorized as a fast algorithm if the compression and/or decompression speed(s) are at least a threshold speed. For example, decompression algorithms may be considered fast algorithms if they decompress medical images at a minimum image rate per time period and/or at a minimum bandwidth per time period. For example, fast algorithms might be defined as those decompression (and/or compression) algorithms that decompress (and/or compress) images at no slower than 20 msec/image. Similarly, fast algorithms might be defined as those decompression (and/or compression) algorithms that decompress (and/or compress) images at no less than 40 MB/sec. In these examples the corresponding slow algorithms would be those algorithms that decompress (and/or compress) images at slower than 20 msec/image and/or less than 40 MB/sec. In some embodiments different thresholds for compression and decompression speeds are considered as the speed of compression and decompression may differ for a particular algorithm. For example, a fast compression algorithm might be defined as one that can compress images at no slower than 40 msec/image and decompress images at no slower than 20 msec/image.

Depending on the embodiment, criteria for categorizing algorithms as fast or slow algorithms may vary based on, for example, characteristics of the particular Information Display Computing Device (e.g., processor speed, video capabilities, etc.), preferences of a viewer (e.g., preferred speed of viewing images, etc.), image characteristics (e.g., exam modality, image size, slice thickness, etc.), etc. Thus, fast (slow) algorithms could vary on an image to image, device to device, viewer to viewer, etc., basis, based on the applicable criteria for categorizing the algorithms. In one embodiment, an algorithm is considered a fast algorithm if it decompresses images at a rate that allows a viewer of the images to view the decompressed images without delays for decompression (e.g., all decompression is done in the background so the viewer doesn't have to wait for any images to be decompressed). For example, a user may determine that the maximum speed at which he views images of a particular modality is N images/second. He may thus set the threshold for categorizing algorithms as fast at a decompression level of at least N images/second. In one embodiment, the threshold speed between fast and slow algorithms is set automatically by the computing device 150, such as based on any one or more of the criteria noted above. For example, a computing device 150 may access historical data regarding viewing speeds of a particular operator and determine a required decompression speed for a requested image series. Alternately, the computing device 150 may access preferences of a user, such as preferences for different modalities, clinical indications, etc., of image series, and select a fast algorithm threshold based on those preferences. In other embodiments, the computing device 150 may automatically determine a fast algorithm threshold based on any other combination of characteristics.

In one embodiment, an algorithm may be categorized as a fast algorithm based only on decompression characteristics, without considering compression characteristics. In other embodiments, algorithms may be categories as fast algorithms based on both decompression and compression characteristics. In those embodiments, the speeds (e.g., MB/sec or msec/image) may be different for decompression and compression operations. For example, a fast algorithm might be defined as an algorithm that compresses images at a rate of at least 30 MB/sec and decompresses images at a rate of at least 40 MB/sec. In this example, an algorithm could be considered a fast algorithm even if the compression rate is slower than the required decompression rate.

Depending on the embodiment, fast algorithms could be a lossless, such as DICOM JPEG lossless compression, or lossy, such as DICOM JPEG lossy compression, depending on the user's preference or other factors.

FIG. 6 is a flowchart illustrating one embodiment of a method of compressing images using a fast algorithm. For purposes of illustration, the method of FIG. 6 is described as performed by a computing system, such as one of the computing systems 150 or 250 that also provide images for display. However, the method may be performed by any other computing system, such as a server, for example. Additionally, while the method of FIG. 6 is described with reference to a single image, some or all of the blocks may be performed concurrently on a plurality of images, such as images of an image series (e.g., a plurality of related images, such as images of CT or MR scan).

In block 305 an image is accessed (e.g., received and/or at least partially read from a storage device) by the computing system. For example, the image may be received from another computing system, e.g., PACS System 136 or Digital Pathology System 146 of FIG. 1. Alternatively, the image may already be stored by the computing system and the method of FIG. 6 may be initiated in response to some indication that the image should be made available for fast viewing, such as manual selection of a series of images including the image by a user of the computing system and/or an automatic selection of the image by an image pre-loading algorithm.

Moving to block 310, the computing device determines whether or not the image is compressed. If the image is not compressed, then the image is compressed using the fast algorithm in block 320 and stored in memory in block 339.

If the computing system determines at block 310 that the input image is already compressed, then at block 330 the computing system determines if the input image is already compressed with a fast algorithm (e.g., a particular fast algorithm or one of a group of acceptable fast algorithms). For example, the computing system may determine a compression technique used to compress the image, such as based on header information of the image file, in order to make a determination as to whether decompression of the image may be performed by a fast algorithm. If the image is compressed with the fast algorithm then it is stored in memory in block 339.

If the computing system determines at block 330 that the compressed input image is not stored using the fast algorithm, it is decompressed in block 335 using the decompression algorithm appropriate to the type of compression used by the image. The uncompressed image is then compressed in block 337 using a fast algorithm and then stored in memory in block 339. In an embodiment where the method of FIG. 6 is performed by a computing system (e.g., PACS server) that transmits images to the computing device, the compressed image may be stored only transitorily on the server in block 339 until/while the image is transmitted to the viewing computing system or other image storage device.

In one embodiment, the method of FIG. 6 is performed by the computing device that has received images, for example a PACS workstation that has received images from a PACS server. In another embodiment, these steps may occur on the PACS server prior to transmission, for example to PACS workstation. For example, the PACS server may choose a fast algorithm based on the characteristics of the PACS workstation and then decompress the images and recompress them with a fast algorithm prior to transmission to the PACS workstation. The PACS server might choose a different fast algorithm for compression of images to be transmitted to a PC-based PACS workstation vs. transmission to a smartphone, such as an iPhone. For example, the method of FIG. 6 may include a determination of a viewing environment (e.g., a type of viewing device and/or a viewer) and may then select a most appropriate fast algorithm based on the type of viewing device, preference of the viewer, or other attributes associated with viewing of the image.

FIG. 7 is a flowchart illustrating one embodiment of a method of decompressing and displaying images that have been compressed. The method of FIG. 7 may be performed by a computing device that has access to images stored in a memory and that displays the images for viewing.

Beginning in block 341, the image compressed using the fast algorithm is accessed in a memory. Typically, the memory is local to the computing device (e.g., RAM of the computing device) so that the image can be quickly accessed. However, the image might be stored in an attached device, such as a memory device that is coupled to the computing device. The compressed image is decompressed using the fast algorithm in block 342 and displayed in block 343.

In another embodiment, the decompressed image is used for a purpose other than, or in addition to, display. For example, the image may be utilized for multiplanar reconstruction (MPR) or 3D volume rendering. In another embodiment, the decompressed image serves as input for a computer aided diagnosis (CAD) system.

In another embodiment, the choice of whether to use in-memory compression is determined by the speed of the fast algorithm on the particular computing device. For example, in-memory compression might be utilized on a particular device only if it is capable of decompressing a 1 megapixel image in less than 50 milliseconds.

In another embodiment, the decision as to what compression algorithm to use is determined by characteristics of the computing device. In the case of two compression algorithms, algorithm A and algorithm B, one computing device might execute algorithm A faster than B while another device might execute algorithm B faster.

In another embodiment, the choice of whether to use in-memory compression would be determined by the amount of free memory. For example, if there is sufficient free memory to store a desired number of images in uncompressed format, in-memory compression might not be utilized. In one embodiment, once free memory drops below a threshold, uncompressed images in memory would be compressed as well as additional images communicated to the computing device.

In another embodiment, the choice of the compression algorithm utilized as the fast compression algorithm would vary depending on the characteristics of each image. For example, one compression algorithm might be used for 16-bit grayscale images that are equal to or less than 1 megapixel in size, another for grayscale 16-bit images that are larger than 1 megapixel in size, and third algorithm for color images. Thus, a series of images having images with different characteristics may include images compressed with different fast algorithms.

Image compression in PACS is typically standards based. For example, the DICOM standard includes the use of the JPEG and JPEG-2000 compression techniques. But in-memory compression as described herein could use any compression technique, particularly if it were lossless, for example to leverage available specialized processors such as CPUs, GPUs and multicore architectures, as well as advanced compression algorithms that have not become standards.

FIG. 8 is a flowchart illustrating one embodiment of a method of decompressing and recompressing images for rapid viewing of the images. In block 402 an image is accessed (e.g., received and/or at least partially read from a storage device) by a computing device on which the image will be displayed (e.g., computing device 150 or 250). In block 404, the computing device determines whether or not to use in-memory compression, for example based on one or more of the factors discussed above. If in-memory compression is not to be used, then in block 406 the computing device determines whether or not the image is compressed. If the image is not compressed then it is stored in memory in block 422. If the image is compressed then it is decompressed in block 408 before being stored in block 422.

If the computing device determines at block 404 that in-memory compression is to be used for the image then the fast compression algorithm is chosen in block 410, for example based on the characteristics of the image and/or the characteristics of the computing device.

In block 412 the computing device determines whether or not the image is already compressed. If it is not compressed, then in block 420 it is compressed using the fast algorithm and then stored in memory in block 422.

If the computing device determines at block 412 that the image is already compressed, then in block 414 the computing device determines whether the image is already compressed by the fast algorithm (or one of multiple acceptable fast algorithms). In one embodiment, there could be more than one fast algorithm so that this condition could be satisfied if the image is already compressed using one of a number of predetermined, acceptable fast algorithms.

If the computing device determines at block 414 that the image is already compressed by an acceptable fast algorithm then the method continues to block 422 where the image is stored in memory without further decompression/compression. If, however, the computing device determines in block 414 that the image is compressed with an algorithm that is not an acceptable fast algorithm, the image is first decompressed in block 416 with an algorithm appropriate to the type of compression. The decompressed image is then compressed with the Fast Compression Algorithm in block 418 prior to storing it in memory in block 422.

Summary

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and partially or fully automated via, software code modules executed by one or more general purpose computers. For example, the methods described herein may be performed by an Information Display Computing Device and/or any other suitable computing device. The methods may be executed on the computing devices in response to execution of software instructions or other executable code read from a tangible computer readable medium. A tangible computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method comprising:
   accessing, by a first computing device including one or more computer processors configured with computer executable instructions, an image compressed at a first compression level;
   determining, by the first computing device in communication with a second computing device, a type of the second computing device;
   determining, by the first computing device and based at least on the type of the second computing device determined by the first computing device, a first decompression speed associated with the second computing device, wherein the first decompression speed indicates a speed at which the second computing device is configured to decompress the image compressed at the first compression level;
   in response to determining that the first decompression speed does not satisfy at least a threshold decompression speed,
      establishing, by the first computing device, a second compression level of the image corresponding to a second decompression speed at which the second computing device is configured to decompress the image compressed at the second compression level, and
      initiating, by the first computing device, storage of the image at the second compression level in an electronic memory; and
   in response to determining that the first decompression speed does satisfy at least the threshold decompression speed, initiating, by the first computing device, storage of the image at the first compression level in the electronic memory.

2. The method of claim 1, wherein determining the first decompression speed associated with the second computing device is further based on at least one of: a processor speed of the second computing device, video capabilities of the second computing device, or decompression capabilities of the second computing device.

3. The method of claim 2, wherein determining the first decompression speed associated with the second computing device is further based on one or more characteristics associated with the image.

4. The method of claim 1 further comprising:
   selecting, by the first computing device and based on the type of the second computing device determined by the first computing device, the threshold decompression speed.

5. The method of claim 4, wherein the threshold decompression speed is selected further based on at least one of: a processor speed of the second computing device, video capabilities of the second computing device, decompression capabilities of the second computing device, preferences of a user of the second computing device, usage patterns of a user of the second computing device, a modality of the image, a size of the image, a slice thickness represented in the image, one or more anatomical structures represented in the image, a color depth of the image, or a bit depth of the image.

6. The method of claim 4, wherein the threshold decompression speed is provided by a user of the first and/or second computing device.

7. The method of claim 1 further comprising:
determining, by the first computing device, the second compression level based on at least one of: a characteristic of the second computing device, a characteristic of a user of the second computing device, and/or a characteristic of the image.

8. The method of claim 7, wherein the at least one of the characteristic of the second computing device, the characteristic of the user of the second computing device, and/or the characteristic of the image used in determining the second compression level include at least one of: a type of the second computing device, a processor speed of the second computing device, video capabilities of the second computing device, decompression capabilities of the second computing device, preferences of a user of the second computing device, usage patterns of a user of the second computing device, a modality of the image, a size of the image, a slice thickness represented in the image, one or more anatomical structures represented in the image, a color depth of the image, or a bit depth of the image.

9. The method of claim 1, wherein establishing the second compression level of the image comprises:
decompressing the image; and
recompressing the image at the second compression level.

10. The method of claim 9, wherein the image is recompressed at the second compression level using a fast compression algorithm.

11. The method of claim 1, wherein the second computing device comprises a mobile computing device.

12. The method of claim 1, wherein the electronic memory is associated with at least one of the first computing device or the second computing device.

13. The method of claim 1, wherein the type of the second computing device includes at least one of: a server, a desktop computer, a workstation, a mobile computer, a smartphone, a tablet computer, a cell phone, a personal digital assistant, a gaming system, a kiosk, or an audio player.

14. A computing system comprising:
a non-transitory computer readable storage medium storing software instructions; and
one or more hardware processors configured to execute the software instructions in order to cause the computing system to:
determine a type of a computing device;
determine, based on the type of the computing device, a first decompression speed associated with the computing device, wherein the first decompression speed indicated a speed at which the computing device is configured to decompress a file compressed at a first compression level;
in response to determining that the first decompression speed does not satisfy a threshold decompression speed,
recompress the file at a second compression level that does satisfy the threshold decompression speed, and initiate storage of the recompressed file in an electronic memory; and
in response to determining that the first decompression speed does satisfy the threshold decompression speed, initiate storage of the file compressed at the first compression level in the electronic memory.

15. The computing system of claim 14, wherein the one or more hardware processors are configured to execute the software instructions in order to further cause the computing system to:
Select the threshold decompression speed based on the type of the computing device.

16. The computing system of claim 15, wherein the threshold decompression speed is selected further based on at least one of: a processor speed of the computing device, video capabilities of the computing device, decompression capabilities of the computing device, preferences of a user of the computing device, usage patterns of a user of the computing device, a modality of the file, a size of the file, a slice thickness represented in the file, one or more anatomical structures represented in the file, a color depth of the file, or a bit depth of the file.

17. The computing system of claim 15, wherein the threshold decompression speed is provided by a user of the computing system and/or the computing device.

18. A non-transitory computer-readable storage medium storing computer-executable instructions that, when executed by a computer system, configure the computer system to perform operations comprising:
accessing an image compressed at a first compression level;
determining a type of a computing device useable to view the image;
determining, based at least on the type of the computing device, a first decompression speed associated with the computing device, wherein the first decompression speed indicates a speed at which the computing device is configured to decompress the image compressed at the first compression level and provide the image for viewing;
in response to determining that the first decompression speed does not satisfy at least a threshold decompression speed,
establishing, based at least on the type of the computing device, a second compression level of the image corresponding to a second decompression speed at which the computing device is configured to decompress the image compressed at the second compression level, and
initiating storage of the image at the second compression level in an electronic memory; and
in response to determining that the first decompression speed does satisfy at least the threshold decompression speed, initiating storage of the image at the first compression level in the electronic memory.

19. The non-transitory computer-readable storage medium of claim 18, wherein determining the first decompression speed associated with the computing device is further based on at least one of: a processor speed of the computing device, video capabilities of the computing device, or decompression capabilities of the computing device.

20. The non-transitory computer-readable storage medium of claim 18, wherein the operations further comprise:

determining the second compression level based on at least one of: a characteristic of the computing device, a characteristic of a user of the computing device, and/or a characteristic of the image.

21. The non-transitory computer-readable storage medium of claim 20, wherein the at least one of the characteristic of the computing device, the characteristic of the user of the computing device, and/or the characteristic of the image used in determining the second compression level include at least one of: a type of the computing device, a processor speed of the computing device, video capabilities of the computing device, decompression capabilities of the computing device, preferences of a user of the computing device, usage patterns of a user of the computing device, a modality of the image, a size of the image, a slice thickness represented in the image, one or more anatomical structures represented in the image, a color depth of the image, or a bit depth of the image.

* * * * *